US006443882B1

(12) United States Patent
Wascher et al.

(10) Patent No.: US 6,443,882 B1
(45) Date of Patent: *Sep. 3, 2002

(54) APPARATUS AND METHOD FOR CREATING A BIOLOGICALLY USEFUL MAGNETIC FIELD

(75) Inventors: Rick R. Wascher, Rock Island; C. Douglas Williams, Signal Mountain; Floyd E. Bouldin, McMinnville, all of TN (US)

(73) Assignee: EMF Therapeutics, Inc., Chattanooga, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/556,450

(22) Filed: Apr. 24, 2000

Related U.S. Application Data

(63) Continuation-in-part of application No. 09/111,769, filed on Jun. 8, 1998, now Pat. No. 6,083,149.

(51) Int. Cl.[7] ............................. A61B 17/52; A61N 2/00
(52) U.S. Cl. ................................................ 600/9
(58) Field of Search ........................ 600/9, 10, 11, 600/12, 13, 14, 15; 335/306

(56) References Cited

U.S. PATENT DOCUMENTS 5,478,303 A * 12/1995 Foley-Nolan et al. ......... 600/15
5,880,661 A * 3/1999 Davidson et al. ............ 335/306
6,083,149 A * 7/2000 Wascher et al. ................ 600/9
6,149,577 A * 11/2000 Bouldin et al. ............... 600/13

\* cited by examiner

Primary Examiner—Kevin Shaver
Assistant Examiner—Brian Szmal
(74) Attorney, Agent, or Firm—Rick R. Wascher

(57) ABSTRACT

A method and apparatus for relieving pain associated with degenerative diseases and disorders in biological subjects such as mammals. The method employs the use of an apparatus which is capable of producing a magnetic field of a particular nature which has been proven in human tests to dramatically reduce pain. An embodiment of the apparatus includes a frame, a plurality of magnets capable of producing a magnetic field wherein each of the plurality of magnets has a north pole and a south pole and a longitudinal axis passing therethrough and are partially held in place by the frame. Another embodiment incorporates a coil of electrically conducting material is wrapped about a frame, and/or the plurality of magnets in an orthogonal relationship to the longitudinal axis of each of the plurality of magnets. A source of electrical energy supplies an electrical current to the coil enabling a magnetic field to be produced therefrom. A switch is provided to enable the electrical current to flow in a first direction and optionally in a second direction opposite to the first direction. A rectifier is provided to alter the inherent supply voltage (e.g., 60 hertz) to a 120 hertz half sine or corresponding DC wave form(s) depending upon the electronics of the various embodiments.

25 Claims, 11 Drawing Sheets

Output from grounded rectifier at 7.5 Amps. (in shop)

Output from ungrounded rectifier at 7.5 Amps. (in shop)

SECION A-A

APPARATUS AND METHOD FOR CREATING A BIOLOGICALLY USEFUL MAGNETIC FIELD

RELATED APPLICATION DATA

This is a continuation in part of co-pending U.S. patent application Ser. No. 09/111,769 which was filed Jun. 8, 1998 now U.S. Pat. No. 6,083,149.

BACKGROUND OF THE INVENTION

1. Field of the Invention

The present inventive discovery is directed to the use of a device capable of producing a substantially contained magnetic field or flux field. The inventive device and related discovery uses a magnetic flux field having a never before seen family of wave form(s) which have been determined to be capable of relieving pain associated with degenerative diseases and disorders in mammals such as humans, inhibiting angiogenesis in tumors and retarding tumor growth.

2. Description of the Related Art

A. Angiogenesis

Angiogenesis may be defined as the formation or the initiation of blood carrying vessel or capillary growth in a biological subjects, particularly mammals.

In mature (non-growing) capillaries the vessel wall is composed of an endothelial cell lining, a basement membrane, and a layer of cells called pericytes which partially surround the endothelium. The pericytes are contained within the same basement membrane as the endothelial cells and occasionally make direct contact with them. (See Background FIG. A).

With reference to Background Art FIG. B, angiogenic factors (the black triangles) bind to endothelial cell receptors and initiate the sequence of angiogenesis. When the endothelial cells are stimulated to grow, they secrete proteases which digest the basement membrane surrounding the vessel. The junctions between endothelial cells are altered allowing cell projections to pass through the space created and the newly formed sprout grows towards the source of the stimulus.

With reference to Background Art FIG. C, continued capillary sprout growth is dependent upon several processes and factors: (i) the stimulus for growth must be maintained; (ii) the endothelial cells must secrete the proteases required to break down the adjacent tissue; (iii) the cells themselves must be capable of movement/migration; and (iv) endothelial cell division must take place to provide the necessary number of cells (this takes place at a site behind the growth front of the sprout). Neighboring blind-ended sprouts then join together to form a capillary loop which later matures into a vessel like the one from which it arose.

Tumors cannot thrive without sufficient nutrition provided by the increased circulation of blood achieved through angiogenesis. Improved wound healing may also be explained by a reduction in angiogenesis. In the wound healing process, excessive angiogenesis is believed to lead to scar formation and inefficient (and thereby slower) healing. Pharmaceutical anti-angiogenic agents have reportedly improved wound healing by limiting angiogenic activity and avoiding pathologic angiogenesis. Pathologic angiogenesis is also present in such diseases as arthritis and autoimmune diseases (such as lupus and colitis). Therefore, it is currently believed that the common effects of an magnetic field are derived by modulating the effects of transforming growth factor beta (TGFb) alone or in combination with some other cellular or ionic effect.

The following list of angiogenic related dependent diseases is not exhaustive, but does include the following: Angiofibroma which is an abnormal formation of blood vessels which are prone to bleeding; Neovascular Glaucoma which is an abnormal growth of blood vessels in the eye; Arteriovenous malformations which is an abnormal communication between arteries and veins; Nonunion fractures which are fractures that will not heal; Lupus, and other Connective Tissue Disorders; Osler-Weber syndrome which is a genetic condition resulting in abnormal blood vessels which are prone to bleeding; Atherosclerotic plaques which is a hardening of the arteries; Psoriasis which is a common chronic skin condition; Corneal graft neovascularization which is a complication of corneal replacement surgery; Pyogenic granuloma which is a common skin lesion composed of blood vessels; Delayed wound healing; Diabetic retinopathy which is a leading cause of blindness in diabetics; Scleroderma which is a form of connective tissue disease; Granulations (burns); Neoplasm which is an abnormal cell growth forming solid tumors; Hemangioma which is a tumor composed of blood vessels; Trachoma which is a leading cause of blindness in some countries; Hypertrophic Scars which is abnormal scar formation; Retrolental fibroplasia which is abnormal growth of blood vessels in the retina; Hemophilic joints which is bleeding joints; Vascular adhesions which is excessive scarring; osteoarthritis and rheumatoid arthritis; macular degeneration; cancerous tumors generally; and pain.

B. Pain

A 1911 definition of pain is a term for the psychological state, which may be generally described as "unpleasantness," arising, for example, from the contemplation of a catastrophe or of moral turpitude, and for physical or psychophysical suffering, a specific sensation localized in a particular part of the body.

The term is used in both senses as the opposite of "pleasure," though it is doubtful whether the antithesis between physical and psychical pleasure can be equally well attested. The investigation of the pleasure-pain phenomena of consciousness has taken a prominent place in psychological and ethical speculations, the terms "hedonics" and "algedonics" being coined to express different aspects of the subject. So in aesthetics attempts have been made to assign to pain a specific psychological function as tending to increase pleasure by contrast, pain, for example, is a necessary element in the tragic.

Scientists have experimented elaborately with a view of the precise localization of pain sensations and pain maps can be drawn showing the exact situation of what are known as pain spots. For such experiments, instruments known as "aesthesiometers" and "algometers" have been devised. The great variety of painful sensations, throbbing, dull, acute, intermittent, stabbing, led to the conclusion among early investigators that pains differ in quality. It is, however, generally agreed that all pain is qualitatively the same though subject to temporal and intensive modification.

Pain can result from any condition that stimulates the body's sensors. However, when pain does not resolve after surgical or medical treatment, it becomes chronic in nature. This intractable pain has no relationship to warning of danger and often leads to dramatic changes in a person's ability to function, to stay productive, and to lead a normal family, occupational, and social life.

The ongoing suffering from intractable pain can result in costly and ineffective medical treatments and needless waste of healthcare dollars. Timely referral for early treatment by a pain medicine physician often may dramatically decrease costs of ongoing care.

The intensity, frequency, and quality of pain varies from person to person and may bear no relationship to the degree of injury or illness. Pain can result from any condition that stimulates special sensors in your body that function to detect pain. Examples of conditions that cause pain include: trauma to skin, tendons, ligaments, muscle, bone, nerves, infections, bleeding, and/or tumors for example.

There are different types of pain as mentioned. Acute pain is the discomfort that alerts you to pay attention to the fact that something is wrong with your body. It helps protect your body from further damage and thus can be beneficial in certain circumstances. Acute pain generally resolves as the underlying problem heals or is treated medically.

When pain does not resolve after medical treatment and is prolonged, generally on the order of a time greater of six weeks as most scholars recognize, it no longer serves to protect your body. This pain is often referred to as chronic pain in addition to the suffering often changes the person's ability to function, stay product, and lead a normal life. Timely visits to a pain center for early treatment by a pain medicine specialist may often reduce or cure chronic pain as is so believed by many experts.

The origin of some pain is neuropathic, while other pain is nociceptive. This is important to know because different treatments will work better for each type of pain. Neuropathic pain is pain that is caused by damage to nerve tissue. It is often felt as a burning or stabbing pain. One example of a neuropathic pain is a "pinched nerve." Nociceptive pain means pain caused by an injury or disease outside the nervous system. It is often an ongoing dull ache or pressure, rather than the sharper, trauma-like pain more characteristic of neuropathic pain. Examples of chronic nociceptive pain include pain from cancer or arthritis.

As we know, acute pain, such as spraining your ankle, acts as a warning signal to harm or possible damage to tissues in your body. It prevents additional damage by alerting you to react and remove the source of pain. However, when pain lasts a long time, over six months, and is not relieved by standard medical management, it is called chronic pain. Chronic pain, the pain signal no longer helps, but hinders your body. Chronic pain may result from a previous injury long since healed or it may have an ongoing cause such as arthritis, cancer, nerve damage, or chronic infection. With chronic pain, normal lifestyles can be restricted or even impossible.

There are certain implications of concepts of consciousness for understanding pain behavior and the definition of pain. Judgements of the nature and severity of pain others may be experiencing are heavily influenced by an observer's preconceptions about the nature of the experience. Our personal sense of conscious experience dictates a search for consciousness characterized by the state of awareness found in competent adults, including constructive memories and thoughts, images and feelings. People incapable of verbally articulating experiences akin to those reported by competent older children and adults are at risk of having other evidence of pain denied, minimized, or ignored. Despite substantial behavioral evidence for pain in the neonate and infant, and findings in indicating destructive immediate and long-term consequences if pain is not controlled, pain in infants and children often continues to be discounted.

An alternative perspective on infant consciousness of pain focusing upon sensory and emotional components is presented. The current prominent definition of pain supports the prejudice favoring adult conceptions of consciousness by emphasizing the importance of self-report in assessing pain. Explanatory notes accompanying this definition also perpetrate the misguided belief that the experience of pain emerges as a product of early life experiences. The case for using non-verbal as well as verbal expression in the process of inferring states of pain is presented.

The specialty of pain medicine is concerned with the prevention, evaluation, diagnosis, and treatment of painful disorders. It is recognized as a specialty by the American Medical Association (AMA). The physician specializing in pain medicine often serves as an educator and consultant to other physicians on the intricacies of helping patients in pain. But mostly, pain medicine physicians provide direct care to patients by evaluating, diagnosing, and treating their various conditions. Treatment includes prescribing medication and rehabilitative services, performing pain-relieving procedures, and counseling patients and their families.

Physicians specializing in pain medicine provide care in a variety of settings and are able to treat the entire range of painful disorders encountered in the delivery of quality health care. Benefits of appropriate treatment includes: reduce suffering of patients and their families, save lives (untreated pain may lead to death by suicide or cardiovascular illness), return the patient to being in charge of their life, allows the patient to become more productive, and shorten recovery time.

The specialty of pain medicine is concerned with the prevention, evaluation, etc., as described above. However, such disorders may have pain in associated symptoms arising from a discrete cause, such as post-operative pain or pain associated with a malignancy, or maybe syndromes in which pain constitutes the primary problem such as neuropathic pains or headaches.

The diagnosis of painful syndromes relies on interpretation of historical data; review of previous laboratory, imaging, and electrodiagnostic studies; behavioral, social, occupational and avocational assessment; interview and examination by the pain specialist; and may require specialized diagnostic procedures, including central and peripheral neural block aid or monitored drug infusions. The special needs of the pediatric or geriatric populations are considered when formulating a comprehensive treatment plan for these patients.

The pain physician serves as a consultant to other physicians but is often the principal treating physician and may prescribe care at various levels, such as direct treatment, prescribing medication, prescribing rehabilitative services, performing pain relieving procedures, counseling of patients and families, coordination of care with other health care providers, and provide consultation services to public and private agencies pursuant to optimal healthcare delivery to the patient suffering from a painful disorder. A pain physician may work in a variety of settings and is competent to treat the entire range of painful disorders encountered in delivery of quality health care.

There are two key examples of painful "syndromes." Fibromyalgia syndrome is a chronic invisible condition that has finally come "out of the closet." Fibromyalgia isn't new, it was described by William Balfore, a surgeon at the University of Edinburgh, in the early 1800's. For many years it was called by different names, including chronic rheumatism, myalgia, and fibrocystitis.

In 1987, the American Medical Association recognized FMS as a true illness and a major cause of disability. Now nearly ten years later it is still too often dismissed as the "newest fad disease." Most physicians lack the training to diagnose and treat it. It is incorrect and a disservice to the patient to lump all soft tissue chronic pain conditions as fibromyalgia. FMS is a chronic, nondegenerative, nonprogressive, noninflammatory, truly systemic pain condition. Diseases have known causes and well-understood mechanisms for producing symptoms. FMS is a syndrome, which means it is a specific set of signs and symptoms that occur together. This does not mean fibromyalgia is any less serious or potentially disabling than a disease. Rheumatoid arthritis, lupus, and other serious afflictions are also syndromes. The term "syndrome" is a measure of our ignorance, not our reflectance of the impact fibromyalgia has on our lives. Laboratory tests for fibromyalgia are valid only to rule out other conditions. There is still no blood test that can accurately identify fibromyalgia.

The official research definition further requires that tender points must be present in all four quadrants of the body, that is, the upper right and left and lower right and left parts of your body. You must have had widespread, more or less continuous pain for at least three months. Tender points can fluctuate and vary from day to day and even hour to hour. Many doctors don't stick close to the "research definition," will consider patients with body-wide flu-like symptoms, multiple tender points, characteristic sleep disruption and resultant fatigue as in fibromyalgia.

Tender points occur in pairs in various parts of the body. Because they occur in pairs, the pain is usually distributed equally on both sides of the body. In traumatic FMS, tender points are often clustered around an injury instead of, or in addition to, the eighteen "official" points. These clusters can also occur around a repetitive strain or a degenerative and/or inflammatory problem such as arthritis. The doctor must be very careful to distinguish traumatic fibromyalgia from myofascial pain syndrome. FMS can occur at any age. Many doctors who are expert diagnosticians of FMS have picked out developing FMS in children at the toddler age. There are also people who develop FMS in their geriatric years. The first trigger points of MPS may occur during birth.

Yet another syndrome somewhat related to FMS is chronic myofascial pain syndrome. Myofascial pain syndrome is now a well accepted disease entity as one can find this term in International Classification of Diseases. It is usually caused by trauma such as strain, sprain, or contusion, inflammatory diseases such as tendonitis, bursitis, synovitis or arthritis, or spinal discogenic diseases such as disc herniation or even just only disc bulging. It can also be caused by the cumulative effect of long-standing repetitive minor trauma or long-standing muscle tension due to poor posture or occupational diseases such as that requiring repetitive use of certain muscle groups or emotional stress.

Certain bands of the muscle fibers respond to the trauma or abnormal stress by tightening. This impairs local circulation leading to the accumulation of metabolic waste products and further tightening occurs. The hyperirritable spots within the taut bands of muscle fibers are called trigger points that are painful upon compression and that can cause characteristic referred pain, tenderness, and autonomic phenomena.

Many medical conditions referred to as perpetuating factors, include mechanical stress, nutritional inadequacies, metabolic and endocrine inadequacies, chronic infections, or psychological factors may effectuate myofascial pain syndrome or may aggravate the severity of myofascial pain syndrome.

The diagnosis of myofascial pain syndrome is based on patients' symptoms and objective findings including consistent and characteristic referred-to pain pattern; focal switch responses in the taut bands of involved muscles; limited range of motion; and, weakness without atrophy. The principal treatment of myofascial pain syndrome is stretching and relaxation of tight muscles to break the vicious cycle. This can usually be done with spray and stretch technique with a fluromethane compound and/or with deep pressure soft tissue massage, combined with thermal therapy with hydrocollator, hot pack, superficial moist heat and/or ultrasound deep heat. Elimination of perpetuating factors if any is also very important to avoid frequent reoccurrence.

In addition, some authorities recommend instruction in consistent performance of a home program in order to facilitate recovery. The home programs usually include self-stretching techniques, maintaining proper postures, and therapeutic exercises. Repeated stretching is usually required if the lesion is chronic in nature.

C. Magnetism

Magnetism is a property of charge in motion and is related to electrical theory. Each individual atom of magnetic substance is, in effect, a tiny magnet with a north pole and a south pole. Magnetic properties of materials may be classified as diamagnetic, paramagnetic, and ferromagnetic. Their classification relates to the manner in which materials react in a magnetic field. For example, certain solids such as iron are strongly attracted to magnets. Such materials are called ferromagnetic.

Magnetism is also related to current flowing in a conductor. A magnetic field surrounds a current carrying conductor according to the well known "right hand rule". Conversely, it is also known that a magnetic field of flux can induce current flow in circuits.

Until now, an apparatus and method of the type herein described capable of producing magnetic fields useful for inhibiting angiogenesis in biological subjects, relieving pain, and retarding tumor growth in mammals was previously unknown and had not been discovered or invented.

Until now, an apparatus and method of the type herein described capable of producing magnetic fields useful for inhibiting angiogenesis and retarding the growth rates of cancerous tumors in biological subjects such as mammals was previously unknown and had not been discovered or invented.

SUMMARY OF THE INVENTION

An embodiment of the present invention is directed to a device for establishing or otherwise creating a magnetic field comprised of magnetic and/or electromagnetic components. The preferred embodiments of the present invention are devices found capable of generating a magnetic field which has proven useful to relieve the symptoms associated with degenerative diseases and disorders, including, pain, swelling, stiffness, etc., and inhibiting angiogenesis, and retarding tumor growth in mammals.

The devices may be configured to include permanent magnets, a coil or plurality of coils of wire conductor, or both (hereinafter "three phase" capability). A magnetic field produced by a permanent magnet source can be said to constitute a first phase. A magnetic field produced solely by a current carrying coil or plurality of coils of wire can be said to constitute a second phase. A magnetic field created from a current carrying wire in conjunction with the magnetic field associated with the permanent magnetic source can be said to constitute a third phase.

The third phase can be further described as "additive" or "opposing". Additive means the direction of the field lines for the permanent magnetic field source and the current carrying coil source are similarly oriented in direction and opposing refers to the situation where the aforementioned field lines are in opposing direction, both with reference to the right hand rule for current carrying wires.

The embodiments of the apparatus of the present invention include: (1) permanent magnets, (2) a current carrying wire for producing a magnetic field around it where the lines of magnetic flux are clockwise or counterclockwise around the wire when viewed from a hypothetical common cross-sectional face, (3) a combination of (1) and (2), so long as a substantially planar magnetic field is produced therefrom; (4) an apparatus configured pursuant to (1), (2) or (3) and capable of generating the wave form shown in FIG. 1E; (5) an apparatus configured pursuant to (1), (2) or (3) and capable of generating the wave form shown in FIG. 1F; and (6) an apparatus configured pursuant to (1), (2), (3), (4) and/or (5) which includes a DC wave form signal of twice the frequency of the incoming AC supply voltage.

The pain relieving embodiments of the present invention were found useful for relieving pain associated with degenerative diseases and disorders including TMJ pain by establishing a contained magnetic field and exposing the pain region to the field. One of the embodiments includes a plurality of permanent magnets oriented in a side by side axis parallel orientation such that the longitudinal axis and poles of a first magnet are placed adjacent to and parallel with the longitudinal axis of an adjacent or second magnet of similar but not necessarily identical configuration or properties.

Another of the embodiments includes a coil of conductor such as a length of wire with a voltage drop applied to its opposing ends. The planar or confined finite nature of the field is attributable, for the most part, to a frame onto which the coil(s) is/are wound or the permanent magnets attached. Thus, the coil is supported by a frame onto which it is wound and the frame may also hold permanent magnets.

Symptomatic relief (e.g., pain, swelling, etc.) through the use of the apparatus of the present invention is believed to be most prominent within the central passage way of the frame and preferably through coil(s), and/or the belt of permanent magnets, where the field can be said to be finite, and substantially planar in nature because it is bounded by the frame. Further studies, however, may also reveal that the magnetic field emanating from the front or rear face (i.e., the spaced apart sides of the frame) is also effective.

The preferred number of coil wire turns may vary but is believed to be optimal from between two hundred (200) and one thousand six hundred (1600) turns of insulated copper wire, because of the heat generated in the coil due to the inherent resistance of the wire to carry a current.

The preferred frame is shaped to form a circle, rectangle, square or other shape, such as the preferred ellipse having a central passageway or opening. An enclosed shape is believed highly preferred in order to establish the desired confined or finite field. Other means of establishing a contained, finite, preferably planar magnetic field, for example a magnetic field generator have a field emitting face or plate, are believed to be more difficult to create and thus less desirable than the frames and geometries of the present invention.

It is important to point out, the terms "finite" and "planar", as well as "contained" are used in a relative sense. That is, the magnetic filed established within the area bounded by the frame (i.e., the passageway) will have a magnetic field which may vary in flux density depending upon the location sampled, but remain confined, finite, and planar with respect to the physical boundary of the frame which defines the size and shape of the treatment passageway.

Within the coil assembly, or belt of magnets, is at least one optional thermal sensor of either the resistance or thermocouple type. The sensor(s) measure and indicate the coil temperature at various points, and allow the operator of the device to monitor the potential decay of the permanent magnets, if any, which may be weakened by the generated heat of the device depending upon their composition.

The preferred power supply incorporates a transformer capable of delivering current within the preferred amperage range of 0–15 amps of current, the corresponding voltage for which would depend upon the number of turns of wire used to form the coil.

The voltage difference applied to the coil is passed through a voltage regulating device preferably in the nature of a full-wave rectifier set. By passing the output of the rectifier through a switch assembly the operator may regulate the applied current, and thus the generated field can be changed at will by the operator. The rectifier converts the applied alternating current to a direct current (DC) with a resulting ripple frequency of 120 pulses per second. The nature of the wave form is, therefore, best described as a modified one half sine wave formation, because the portion of the wave below the base line dividing the wave form is inverted upward above thereby resulting in the 120 pulses a second.

Of course, the 120 pulses a second presumes a 60 cycle supply voltage common in the United States, but may also be a 50 cycle supply voltage which is common in Europe thereby giving rise to 100 pulses per second frequency or other supply voltage that proves useful. In fact, it is believed by some that frequency modulation will enhance the beneficial results of the inventive method and apparatus.

With respect to the embodiment of the present invention which includes the optional permanent magnets, at least one magnet is removed from the plurality in order to create a gap in the elliptical string thereof. Physically leaving out magnets during the assembly process and replacing them with non-magnetic material or simply providing an air space insures the magnets themselves do not become current carrying conductors and destroy or unnecessarily affect their integrity during operation of the device.

A cover is attached to the frame to shield the coil. The cover, for example, may be a cooperating cover and frame sized to establish a passage between the coil and the cover to form at least one duct enabling gaseous flow into and out of the passage from a location outside of the passage.

The method of the present invention may be summarized in a variety of ways, one of which is the following: a method of relieving pain associated with degenerative diseases and disorders comprising the steps of: providing a DC magnetic field generating device having three phase magnetic field generating capability including a magnetic field component generated by a current carrying coil; energizing the current carrying coil enabling the DC magnetic field to be concentrated within a substantially planar area defined by a central passageway of a device frame; and placing a biological subject in the DC magnetic field and exposing the biological subject to said DC magnetic field.

The method has been found useful for relieving pain associated with degenerative diseases and disorders categorized within the pain group consisting of: myofacial pain, plantar fascitis, back, leg and neck pain. The preferred method also includes providing a combined DC magnetic field generating device with a plurality of turns of wire and a plurality of permanent magnets; applying an electrical voltage drop across the ends of the wire with the current being greater than 1 amp and less than 15 amps, but preferably between 5 amps and 10 amps.

The apparatus of the present invention may be summarized in a variety of ways, one of which is the following: an apparatus for relieving pain associated with degenerative diseases and disorders in humans, comprising means for producing a magnetic field, wherein the means includes a frame having a continuous sidewall and a central passageway extending therethrough, a coil made of electrically conducting material wrapped about the frame and the central passageway; and a source of DC electrical energy operably connected to the coil for supplying DC electrical current to the coil and establishing a DC magnetic field concentrated within a substantially planar area defined by the central passageway and bounded by the frame. A cover is attached to the frame to shield the coil.

An optional switch capable of regulating the direction of the current flow through the wire is also preferred, and the frame is substantially elliptical. Instead of a single coil, a plurality of coils may be used. The at least one coil has preferably between 200 and 800 turns of wire.

The apparatus may also be summarized as an apparatus for relieving pain, inhibiting angiogenesis in tumors and retarding tumor growth in biological subjects comprising a means for producing a DC magnetic field concentrated within a substantially confined area, wherein the means includes: a frame having spaced apart sides and a central passageway extending therethrough; a coil made of electrically conducting material wrapped about the frame to overlie the central passageway; and a source of DC electrical energy operably connected to the coil for supplying DC electrical current to the coil to establish a DC magnetic field concentrated within a substantially planar area defined by the central passageway and bounded by the frame.

A plurality of optional magnets are positioned adjacent the coil and constrained from movement by the frame, wherein each of the plurality of magnets has a north pole and a south pole and a longitudinal axis passing therethrough, the plurality of magnets are positioned in a side by side axis parallel orientation and are partially held in place by the frame. In the preferred arrangement, the plurality of magnets are positioned to enable the like poles of a majority of the plurality of magnets to be adjacent one another.

The present invention also includes a means for producing a substantially planar, contained, magnetic field capable of relieving pain associated with degenerative diseases and disorders in humans, inhibiting angiogenesis and retarding tumor growth in mammals comprising: a frame having spaced apart sides, a central passageway formed through, and bounded by, each of the spaced apart sides of the frame to define a substantially planar area within the frame; a coil made of electrically conducting material wrapped about the frame and contained within the spaced apart sides; and a source of DC electrical energy operably connected to the coil for supplying DC electrical current to the coil to establish a DC magnetic field concentrated within the substantially planar area.

In addition, the present invention may also be summarized as follows: a device for relieving pain associated with degenerative diseases and disorders such as myofacial pain, plantar fascitis, back, leg and neck pain, inhibiting angiogenesis in tumors and tumor growth comprising: a frame having spaced apart side defining a central passageway and a substantially planar area thereof confined within the frame and bounded by an inside edges of each of the spaced apart sides; coil means including a source of DC electrical energy operably connected to at least one coil of electrically conducting wire enabling a DC electrical current to be applied to the wire for establishing a DC magnetic field concentrated within the substantially planar area defined by the central passageway and bounded by the frame.

The present invention may also be summarized as follows: a method of affecting pain and angiogenesis in tumors of biological subjects comprising the steps of providing a magnetic field generating device having a frame defining a central passageway and a coil of wire wrapped about the frame; producing a magnetic field from the generating device by energizing the coil with electrical energy to produce a wave form of the general type shown in FIG. 1E; and placing a biological subject in the central passageway such that the coil surrounds the biological subject, and exposing the biological subject to the field.

In addition, the invention may also be summarized as: a method of affecting pain and angiogenesis in tumors of biological subjects comprising the steps of providing a magnetic field generating device having a frame defining a central passageway and a coil of wire wrapped about the frame; producing a magnetic field from the generating device by energizing the coil with electrical energy to produce a wave form of the general type shown in FIG. 1F; and placing a biological subject in the central passageway such that the coil surrounds the biological subject, and exposing the biological subject to the field.

The apparatus of the present invention may also be summarized as follows: a device for relieving pain in mammals, comprising means for producing a magnetic field, wherein the means includes a frame having a central passageway, a coil made of electrically conducting material wrapped about the frame and surrounding the central passageway; a source of electrical energy for supplying an electrical voltage and current to the conducting material to create a magnetic field therefrom; and wherein the wave form of the electrical energy is of the general type shown in FIG. 1E.

In addition, the apparatus of the present invention may also be summarized as a device for inhibiting angiogenesis and retarding tumor growth in mammals, comprising: means for producing a magnetic field, wherein the means includes a frame having a central passageway, a coil made of electrically conducting material wrapped about the frame and surrounding the central passageway; a source of electrical energy for supplying an electrical voltage and current to the conducting material to create a magnetic field therefrom.; and wherein the wave form of the electrical energy is of the general type shown in FIG. 1F.

All of the objects, features, and advantages of the present invention are believed to be within the scope of the present invention, even though they are not specifically set forth in this document.

BRIEF DESCRIPTION OF THE DRAWINGS

FIG. 6A–9A are enlarged sectional views of the portion of the embodiment bounded by the dashed viewing circle of FIG. 3 and further including a cover component; and FIG. 6B—9B are enlarged sectional views of the portion of the embodiment bounded by the dashed viewing circle of FIG. 5 and further including a cover component.

DETAILED DESCRIPTION OF THE PREFERRED EMBODIMENT(S)

Figure 1A:
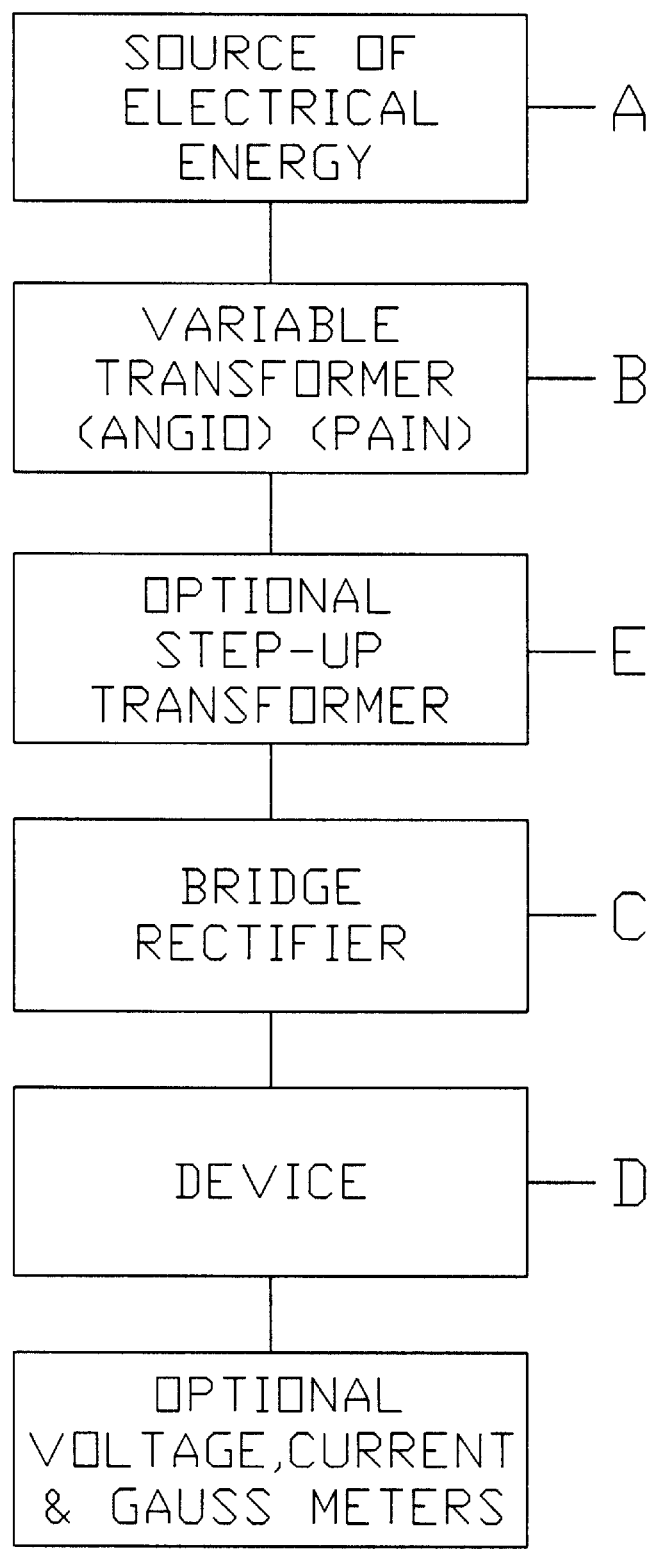
FIGS. 1A and 1B are schematic block diagrams of the electrical components of the present invention.
Figure 1B:
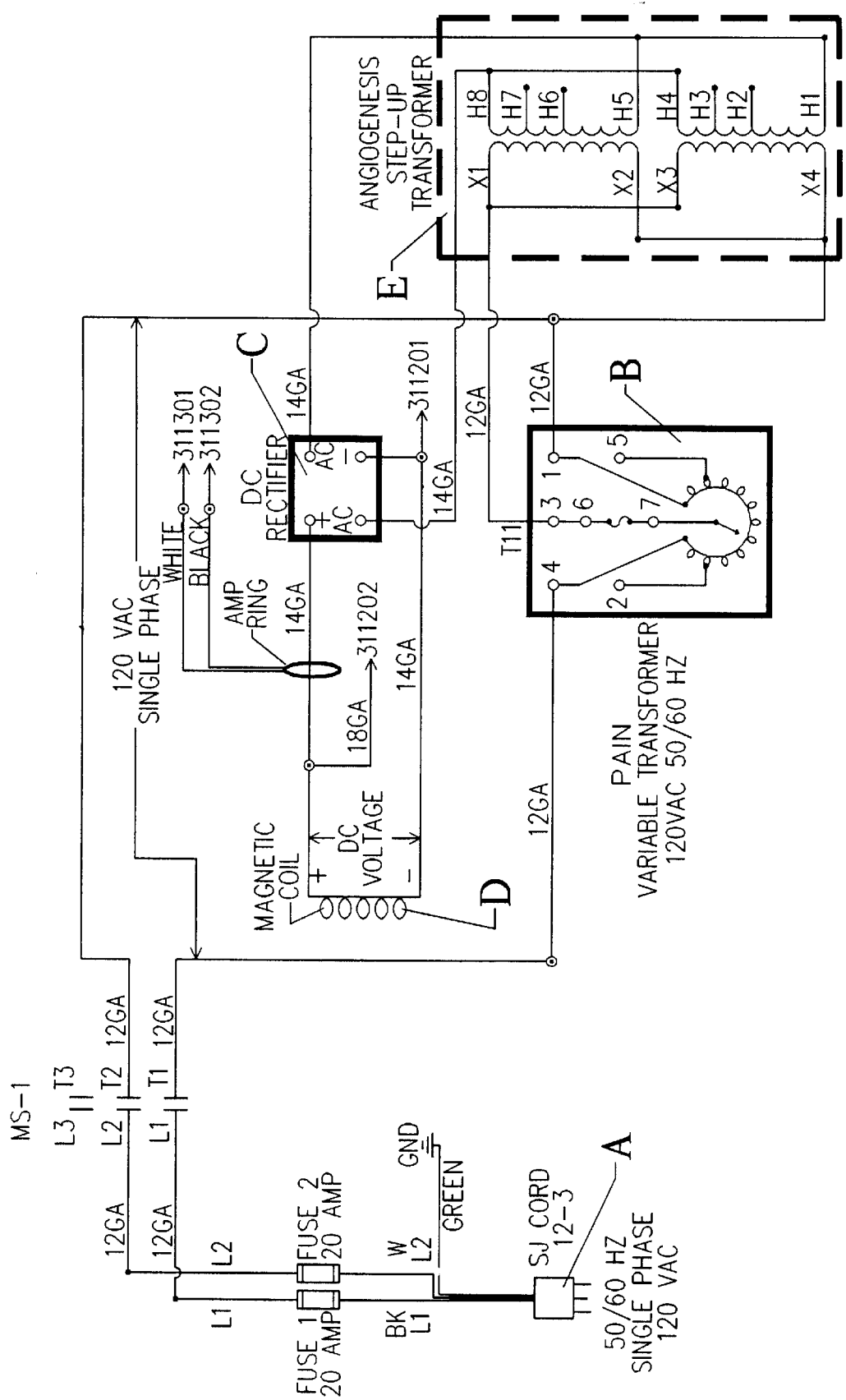

With reference to the schematic diagrams designated as FIGS. 1A and 1B, a source of electrical energy, preferably 110 or 220 volts in the United States, is designated generally by the reference letter A. An AC variable transformer, designated generally by the reference letter B, is electrically connected to the source A by a conventional power cord preferably rated to handle the input voltage of the source.

The transformer varies the AC input voltage. The AC output is then passed through an optional single or optional series of bridge rectifiers C (i.e., labeled as BRIDGE RECTIFIER). The bridge rectifier(s) preferably provide either a half wave or full wave rectification of the wave form to a 60 or 120 cycles per second DC positive (i.e., above the reference line on a sinusoidal oscilloscope) wave form. Of course, in Europe where the supply current is 50 hertz, the resulting half and full wave rectification yields 50 and 100 cycles per second DC.

Figure 1C:
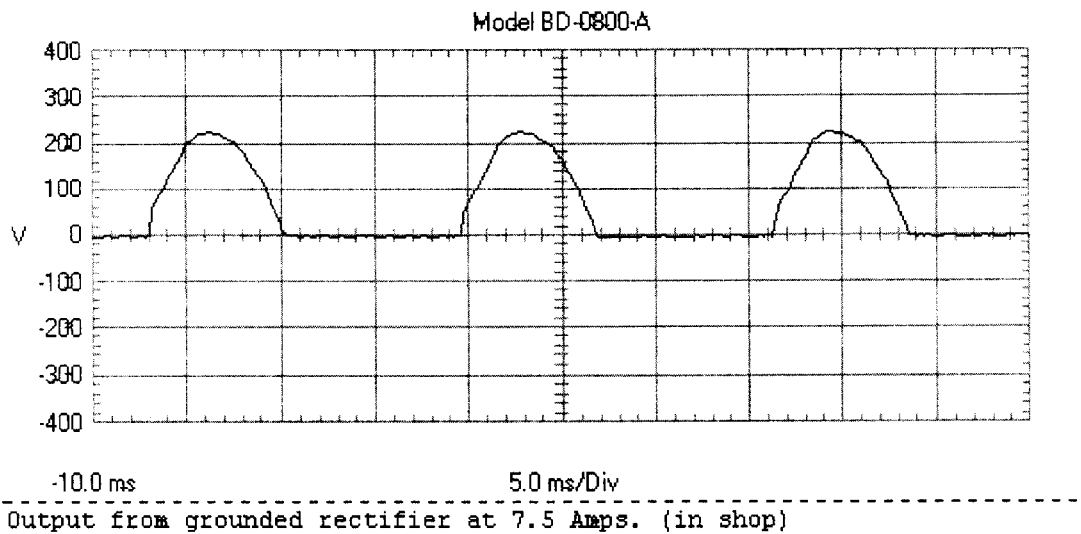
FIG. 1C is a graph illustrating the half rectified wave form produced by an embodiment of the present invention.
Figure 1D:
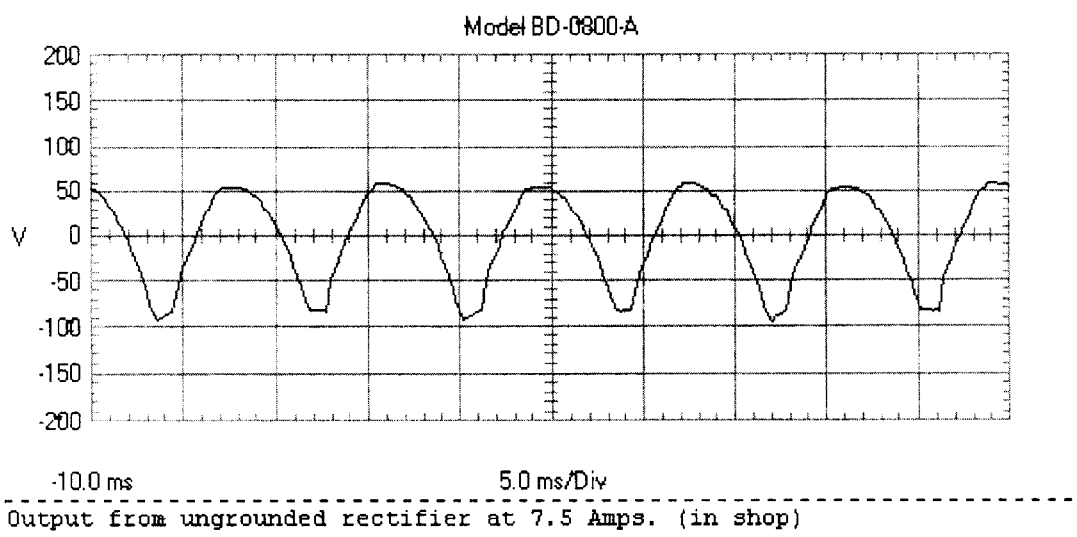
FIG. 1D is a graph illustrating the fully rectified wave form produced by an embodiment of the present invention.

The fully rectified wave form from the bridge rectifier(s) is then passed to the free ends of the coil designated generally by the reference letter D and labeled DEVICE for convenience. FIGS. 1C and 1D are graphs illustrating the half rectified and fully rectified, respectively, wave form produced by an eight hundred (800) winding embodiment of the present invention. The sample graphs were taken when the field strength within the confines of the embodiment tested was to produce 7.5 amps of current.

Optional step-up transformer, designated generally by the reference letter E, is used to alter the resultant signal emitted by the device. For example, the wave form shown in FIG. 1E was produced with the optional step-up transformer E, and the wave form of FIG. 1F was produced without the step-up transformer. The difference in wave forms is believed to present different biological effects of the device.

Figure 1E:
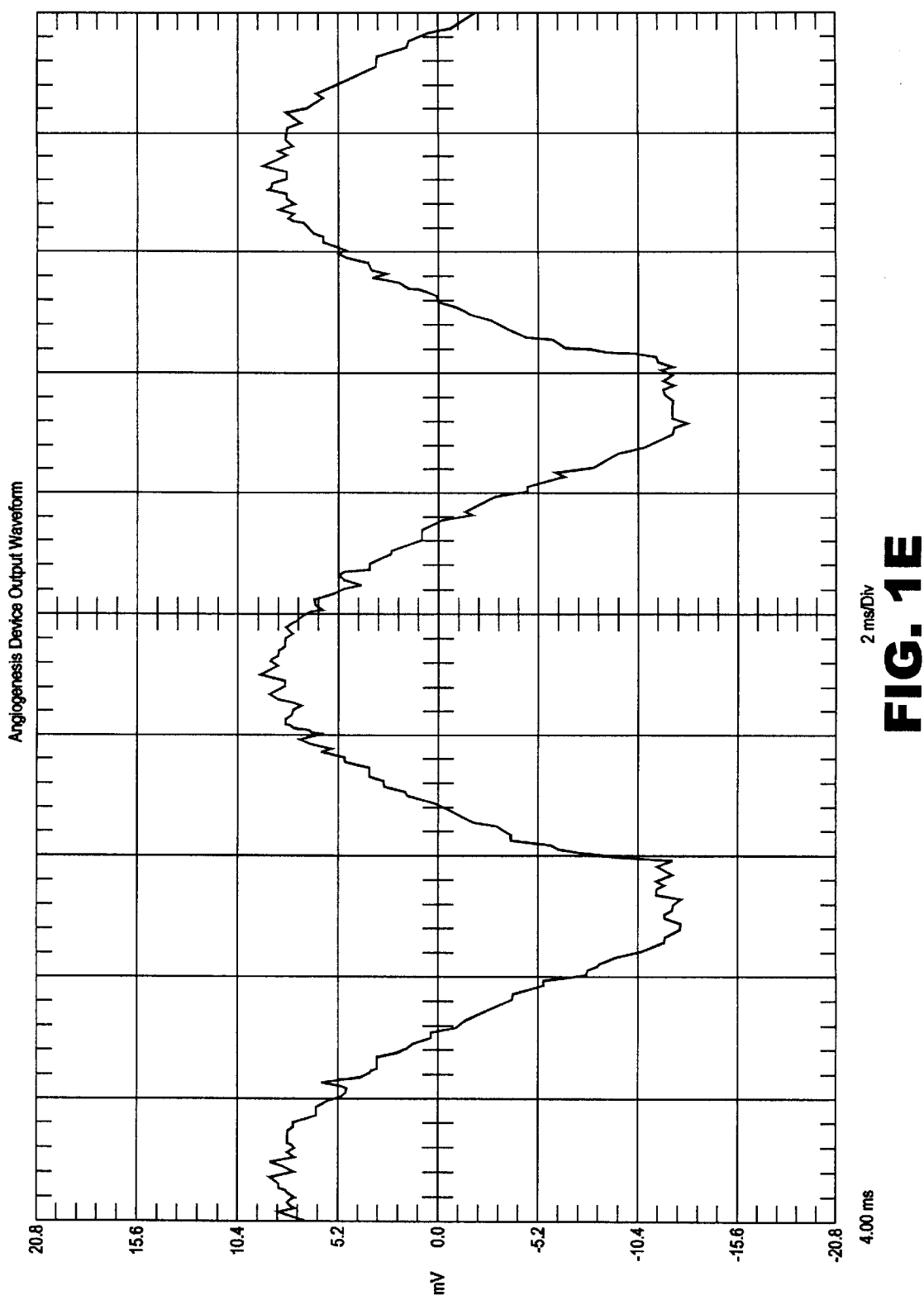
FIG. 1E is a graph illustrating the signal wave generated by an embodiment of the present invention.
Figure 1F:
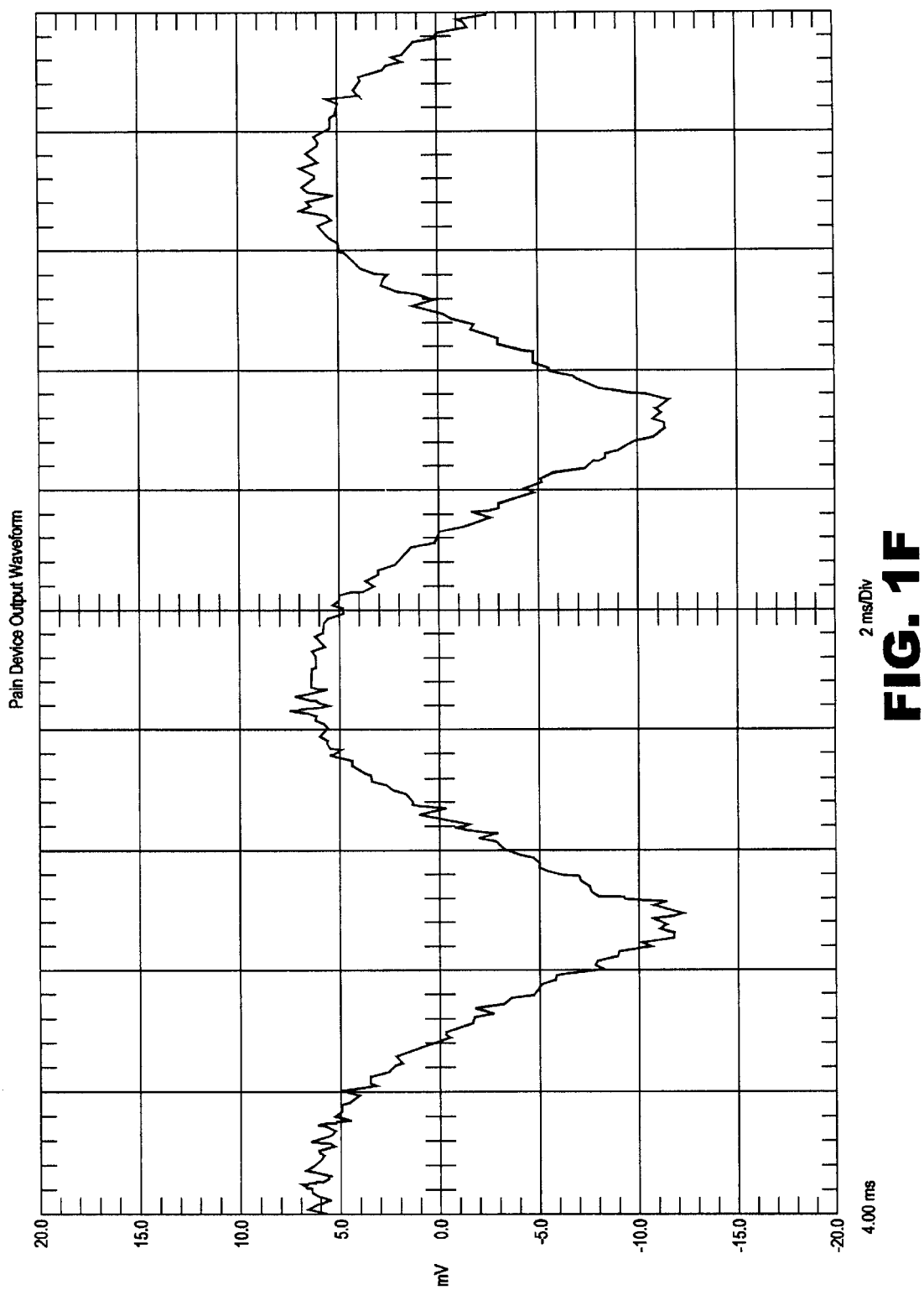
FIG. 1F is a graph illustrating the signal wave for generated by another embodiment of the present invention.

FIG. 1E is a graph of the preferred signal wave form found useful for treating angiogenesis. FIG. 1F is a graph of the preferred signal wave form found useful for treating pain.

The angiogenesis and pain wave forms are fully rectified DC wave forms having twice the frequency of the incoming supply voltage. For example, in the United States of America where the AC input voltage is 110 volts and the frequency is 60 hertz (i.e., cycles per second) the preferred angiogenesis and pain wave forms are 120 cycles per second. Similarly, in Europe where the input voltage has an associated 50 hertz (i.e., cycles per second) the fully rectified DC angiogenesis and pain wave forms would have a frequency of 100 cycles per second.

Figure 2:
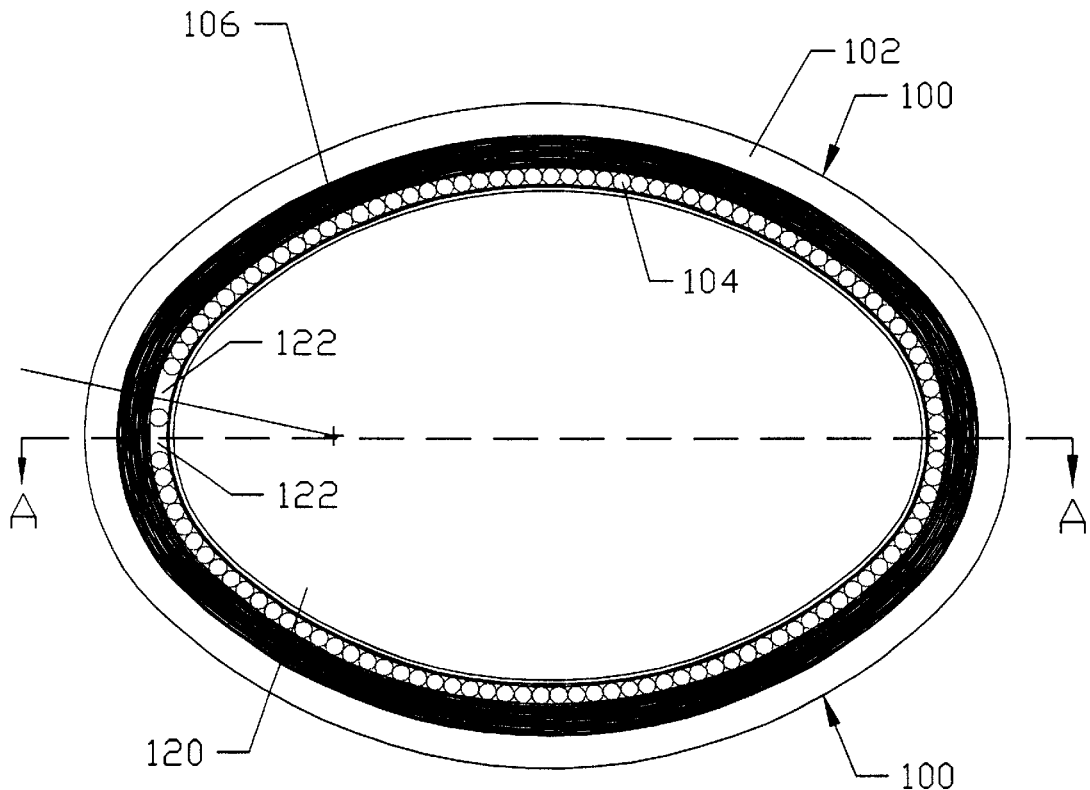
FIG. 2 is a side view of an embodiment of the present invention showing the relative orientation of the optional permanent magnet components and coil component and having a portion of the frame removed for clarity.
Figure 3:
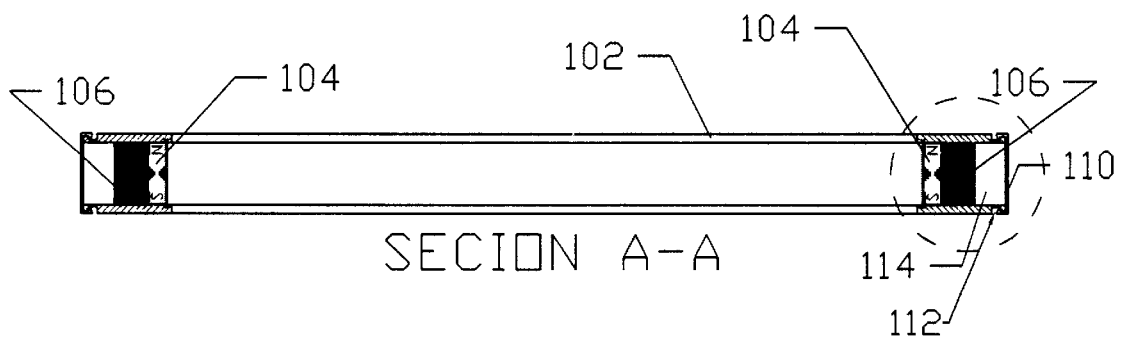
FIG. 3 is a cross-sectional view taken along line A—A of FIG. 2.

With reference to FIGS. 2 and 3, an embodiment of the device component of the present invention is designated generally by the reference number 100. A portion of the device frame 102 has been partially removed from FIG. 2 in order to show the permanent magnets 104 and the interiorly wrapped coil 106 in their preferred orientation. The coil winding 106 overlies the belt or annular layer of permanent magnets 104. A cover 110 is provided as a means of protecting and shielding the coil 106 during operation.

Within the coil assembly are a plurality of optional thermal sensors (not shown in FIGS. 2 and 3), of either resistance or thermocouple type which measure and indicate the coil temperature at various points.

Cover 110 can be a section of raceway cover which includes a cooperating tongue and groove snap connection 112 or any other suitable means of affixation to the frame. As such, the existence of the cover attached to the device frame 102 and the disposition of the magnet and/or coil establish an air space 114 (FIG. 3) between the frame 102, coil 106 and cover 110. The air space 114 provides a means of convective heat transfer such that if an air flow in the air space 114 were created, the flow of air would have a tendency to cool the coil 106 and magnets 104 when they become heated after the coil 106 in energized in the manner described below.

The orientation of the coil 106 and the magnets 104 is readily observed. Cross-section line A—A, which also serves as a vertical axis and horizontal line L, which serves as a horizontal axis, define the centroid of the interior channel 120 of the device. As shown in FIG. 2, there are a pair of gaps 122 in the annular layer or belt of magnets 104. The gaps are provided so as to establish an open circuit condition in case the magnets themselves which are typically made of some metal do become conductors by virtue of their close proximity to the coil.

Figure 4:
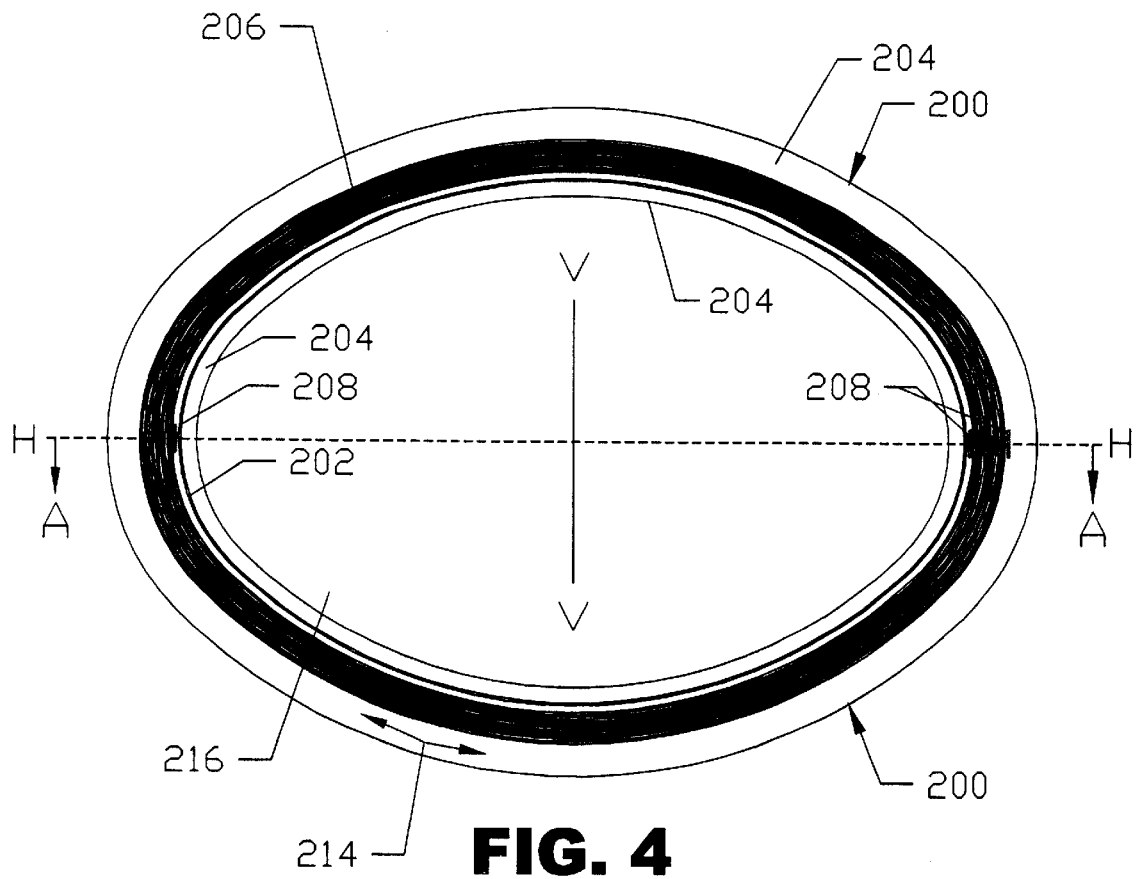
FIG. 4 is side view of the preferred embodiment of the present invention showing the relative orientation of the coil component and without permanent magnets and having a portion of the frame removed for clarity.
Figure 5:
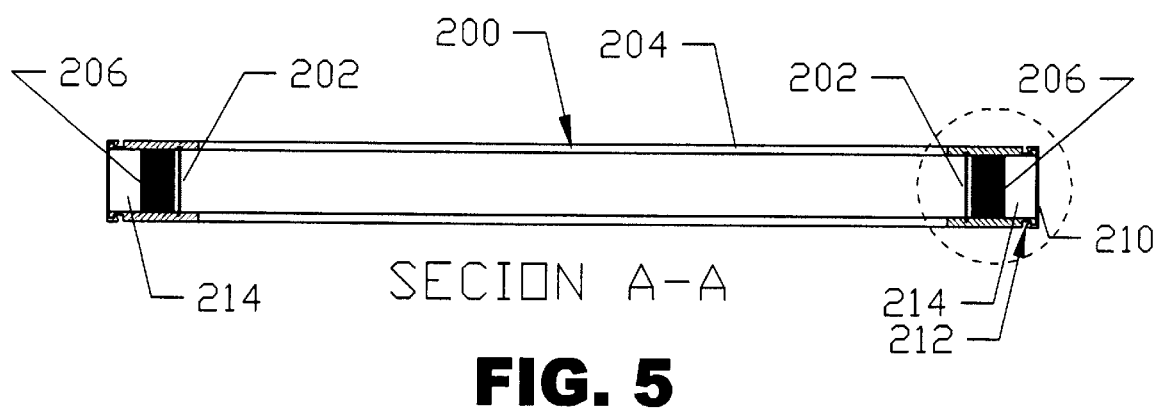
FIG. 5 is a cross-sectional view of the preferred embodiment taken along line A—A of FIG. 4.

With reference to FIGS. 4–5, the preferred embodiment of the coil assembly of the present invention is designated generally by the reference numeral 200. Embodiment 200 includes a frame component 202. The side plates 204 (see FIGS. 3–7B) cover the coil 206 as it is wrapped around the frame 202. One of the side plates has been removed from FIG. 2 for visual clarity of the coil 206 but the side plates 204 are preferably rigidly attached to the frame 202 in a working embodiment of the invention.

Within the coil assembly 204 are a plurality of optional thermal sensors 208, of either the resistance or thermocouple type. The sensors are provided as a way of measuring the coil temperature at various points but do not affect the operation of the invention and its useful effect (i.e., angiogenesis and growth retardation of cancerous tumors).

A cover 210 is preferably rigidly secured to the frame. Attachment of the cover 210 to the frame 202 in the manner shown in the figures creates an air space 214 between the coil 206 and cover 210. The cover 210 may be snapped in place by a snap fit cooperation of the cover and the frame 212, or in the alternative the cover may be rigidly and securely attached by numerous others means of securement. The air space 214 allows for convective heat transfer from the coil 206 to the air within the air space 214. If an air flow is induced in the air space 214, the flow of air would have a tendency to cool the coil 206 if it heats up during use.

Cross-section line A—A of FIG. 4, which also serves as a vertical axis V intersects the horizontal axis H to define an approximate interior centroid of the interior 216 of the device (FIG. 4). When a current flow is induced into the coil 206, a magnetic field around the coil is established pursuant to the right hand rule. The magnetic lines of flux (not shown) are either to the left or to the right depending upon the frame of reference and the direction of current flow in the coil 206.

Figure 6A:
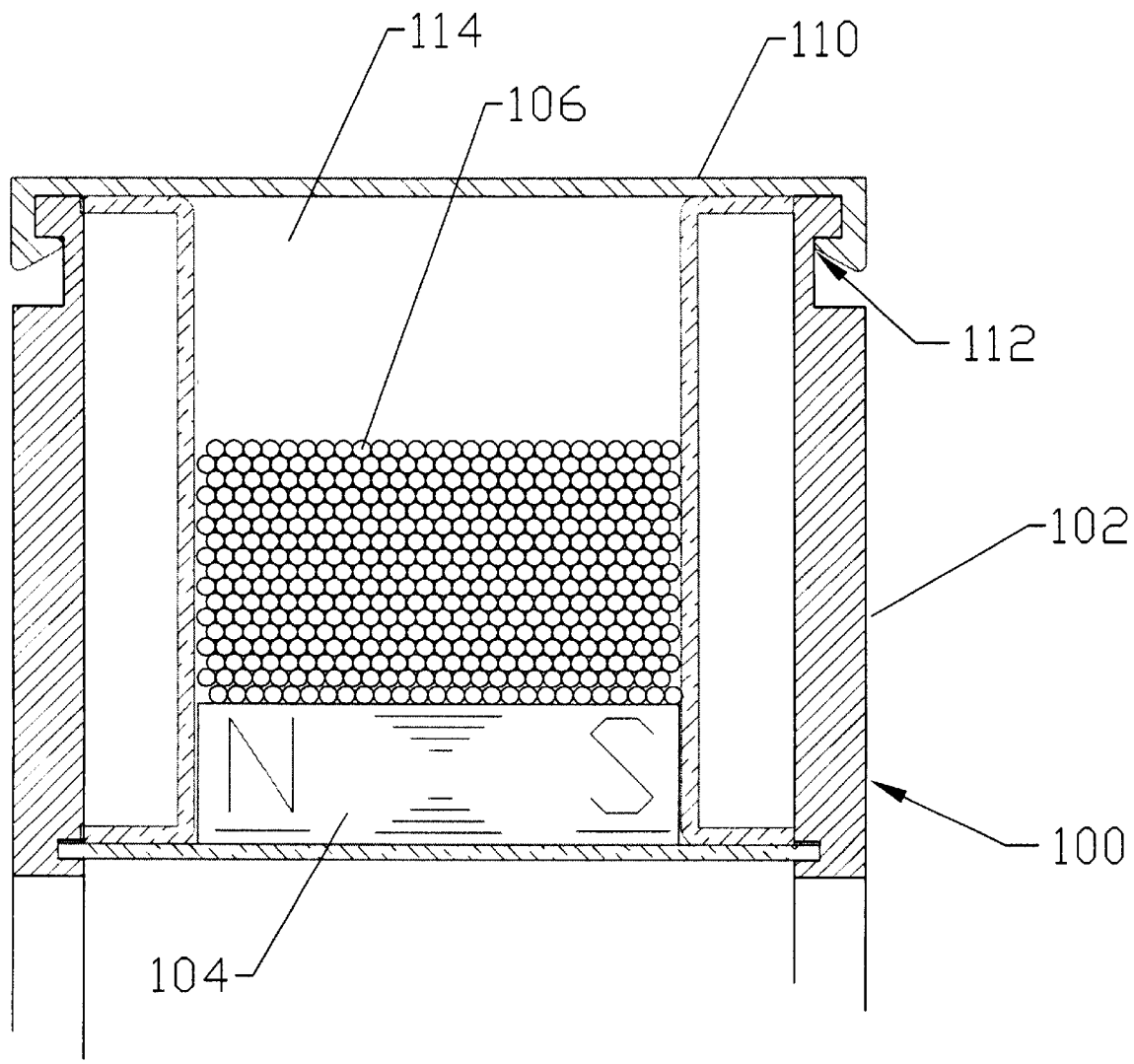
Figure 9A:
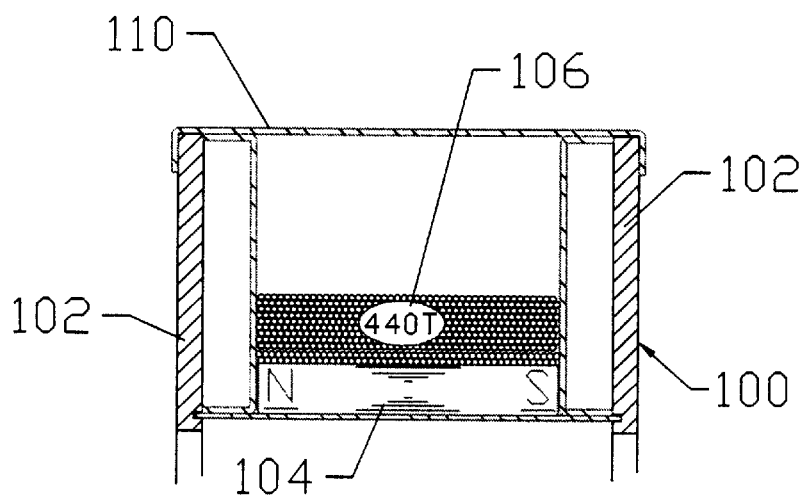
Figure 7B:
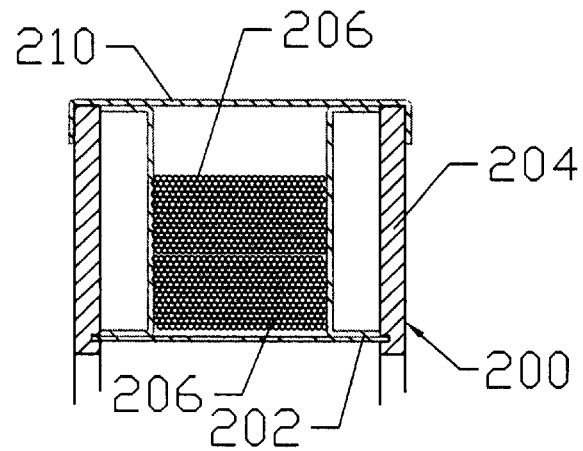
Figure 8B:
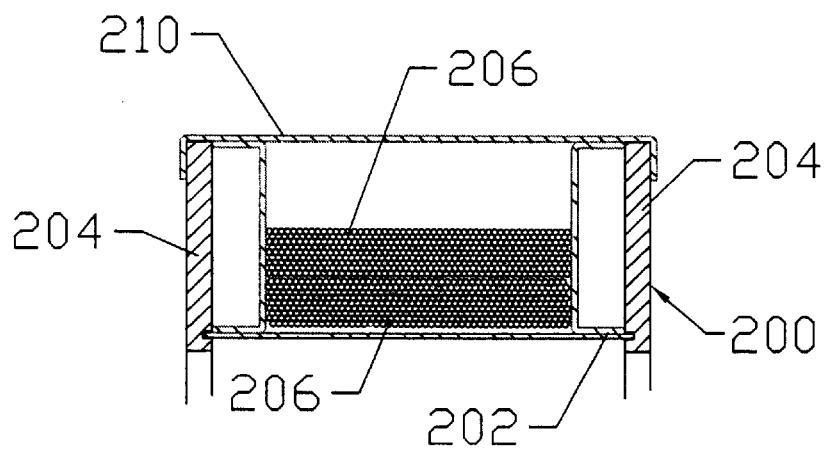

FIGS. 6A–9A illustrate a variety of device profiles in order to demonstrate the various configurations the coil 106 may have depending upon the width of the frame. As shown in FIGS. 6A and 9A, the device may also include multiple coils 106, as well as permanent magnets 104, wherein the figures show the preferred positioning of the magnet(s) in a stacked or adjacent relationship to the coil(s). An optimum coil thickness with respect to width is believed to help establish a more uniform minimum heat generation within the coil 106.

Figure 6B:
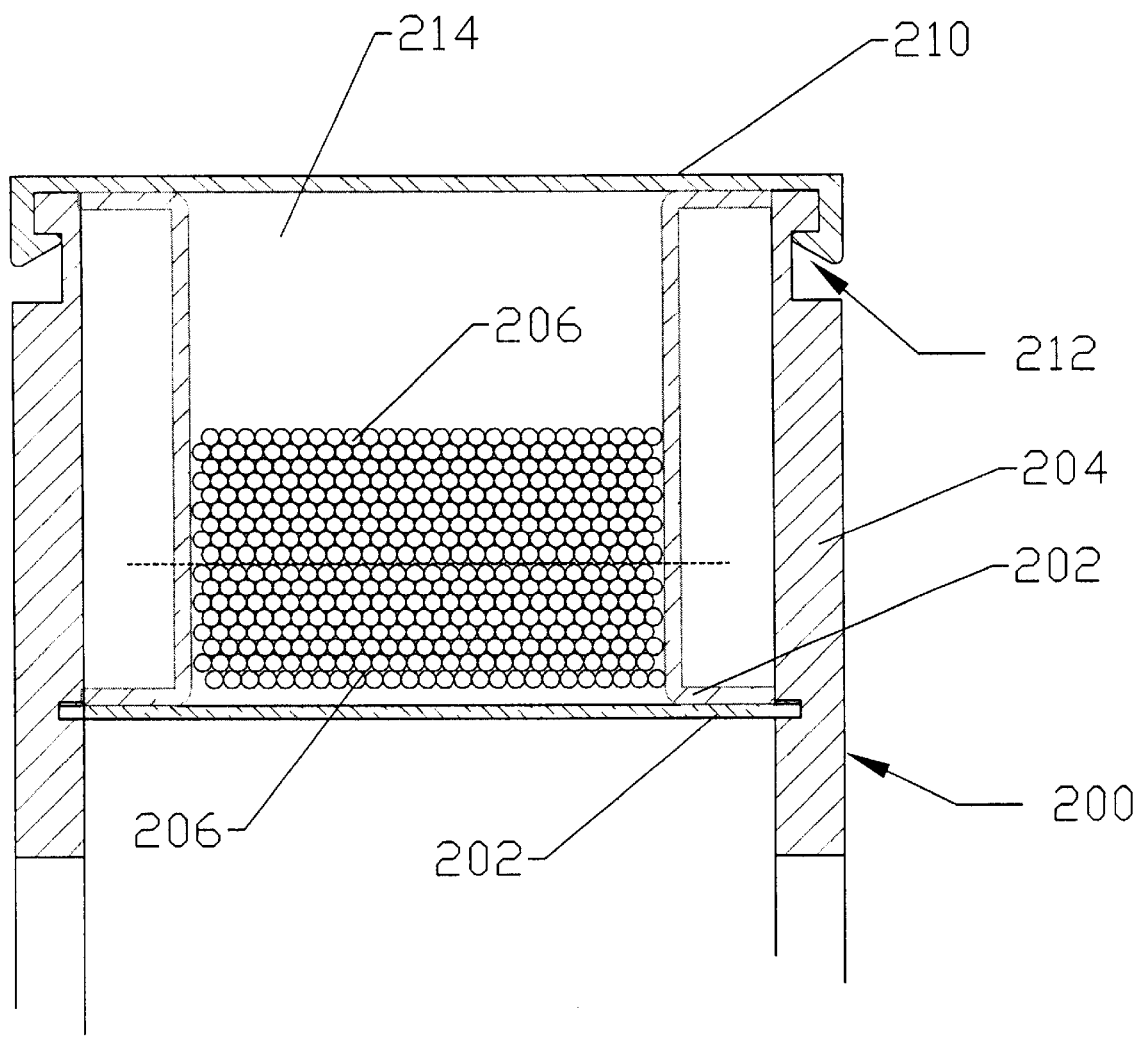
Figure 7A:
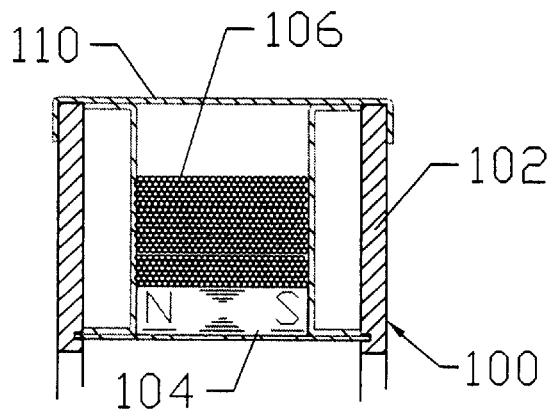
Figure 8A:
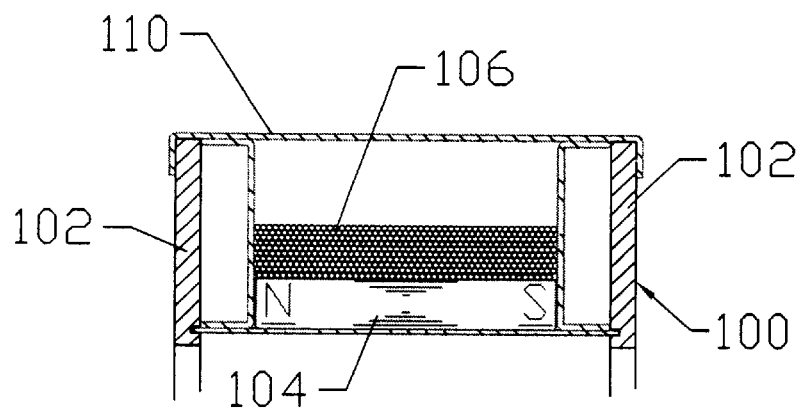
Figure 9B:
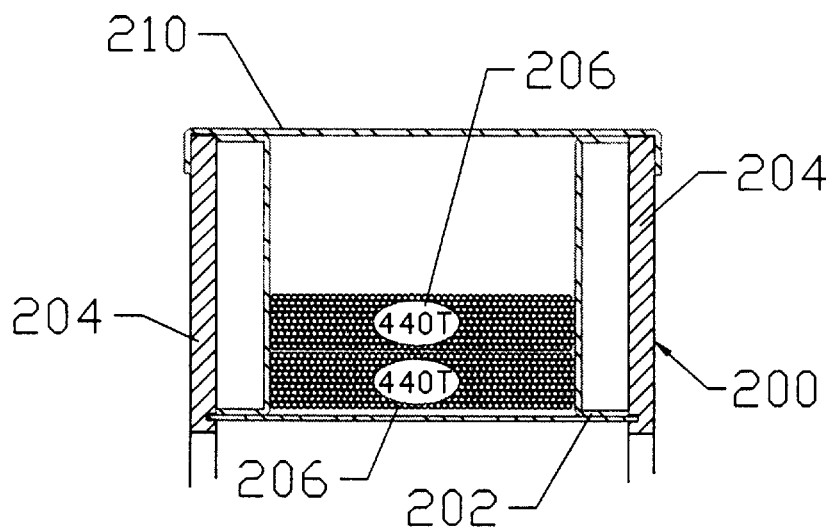

With reference to FIGS. 6B–9B a variety of device profiles are provided in order to demonstrate the various configurations the coil 206 depending upon the width of the frame. As shown in FIGS. 6B and 9B, the device may also multiple coils 206 in a stacked or adjacent relationship as denoted by the hypothetical dashed dividing line of those figures. An optimum coil thickness with respect to width is believed to help establish a more uniform minimum heat generation within the coil 206.

What is claimed is:

1. A method of affecting pain and tumor angiogenesis in biological subjects comprising the steps of:
   providing a magnetic field generating device having a frame defining a central passageway and a coil of wire wrapped about the frame;
   producing a magnetic field from the generating device by energizing the coil with electrical energy to produce a DC wave form signal having twice the number of pulses per second as a frequency of an incoming AC supply voltage; and
   placing a biological subject in the central passageway such that the coil surrounds the biological subject, and exposing the biological subject to the field.

2. The method of claim 1, wherein:
   the method of affecting pain and angiogenesis is a method of inhibiting the rate of angiogenesis in tumor tissue and the magnetic field generating device includes a step-up transformer.

3. The method of claim 1, further comprising the step of:
   providing a magnetic field generating device having between 200 and 1600 turns of wire.

4. The method of claim 1, further comprising the step of:
   applying an electric current to the wire in the range of more than 1 amp and less than 15 amps.

5. The method of claim 1, further comprising the step of:
   providing a magnetic field generating device having three phase magnetic field generating capability.

6. A method of affecting pain and tumor angiogenesis in biological subjects comprising the steps of:
   providing a magnetic field generating device having a frame defining a central passageway and a coil of wire wrapped about the frame;
   producing a magnetic field from the generating device by energizing the coil with electrical energy to produce a DC wave form signal having twice the number of pulses per second as a frequency of an incoming AC supply voltage; and
   placing a biological subject in the central passageway such that the coil surrounds the biological subject, and exposing the biological subject to the field.

7. The method of claim 6, wherein:
   the method of affecting angiogenesis is a method of inhibiting the rate of angiogenesis in tumor tissue.

8. The method of claim 6, further comprising the step of:
   providing a magnetic field generating device having between 200 and 1600 turns of wire.

9. The method of claim 6, further comprising the step of:
   applying an electric current to the wire in the range of more than 1 amp and less than 15 amps.

10. The method of claim 6, further comprising the step of:
    providing a magnetic field generating device having three phase magnetic field generating capability.

11. A device for relieving pain in mammals, comprising:
    means for producing a magnetic field, wherein the means includes:
      a frame having a central passageway,
      a coil made of electrically conducting material wrapped about the frame and surrounding the central passageway;
      a source of electrical energy for supplying an electrical voltage and current to the conducting material to create a magnetic field therefrom; and
      wherein a DC wave form signal having twice the number of pulses per second as a frequency of an incoming AC supply voltage is emitted by the device during operation.

12. The device of claim 11, further comprising:
    a cover attached to the frame to shield the coil.

13. The device of claim 11, further comprising:
    a switch capable of regulating the current flow through the wire.

14. The device of claim 11, wherein the device further includes:
    a step-up transformer in combination with a variable transformer which enable a preferred angiogenesis inhibiting wave form to be produced.

15. The device of claim 11, further including:
    a substantially elliptical frame.

16. The device of claim 11, such that the coil of electrically conducting material wrapped about the frame, further comprises:
    a plurality of coils.

17. The device of claim 11, such that the coil of electrically conducting material wrapped about the frame, further comprises:
    at least one coil having between 200 and 1600 turns of wire.

18. The device of claim 11, further comprising:
    a plurality of magnets situated adjacent the coil of electrically conducting material.

19. A device for inhibiting angiogenesis and retarding tumor growth in mammals, comprising:
    means for producing a magnetic field, wherein the means includes:
      a frame having a central passageway,
      a coil made of electrically conducting material wrapped about the frame and surrounding the central passageway;
      a source of electrical energy for supplying an electrical voltage and current to the conducting material to create a magnetic field therefrom; and
      wherein a DC wave form signal having twice the number of pulses per second as a frequency of an incoming AC supply voltage is produced thereby.

20. The device of claim 19, further comprising:

a cover attached to the frame to shield the coil.

21. The device of claim 19, further comprising:

a switch capable of regulating the current flow through the wire.

22. The device of claim 19, wherein:

a variable transformer which enables an angiogenesis inhibiting wave form to be produced therefrom.

23. The device of claim 19, further including:

a substantially elliptical frame.

24. The device of claim 19, such that the coil of electrically conducting material wrapped about the frame, further comprises:

a plurality of coils.

25. The device of claim 19, further comprising:

a plurality of magnets situated adjacent the coil of electrically conducting material.

* * * * *